United States Patent [19]

Gipson

[11] 3,954,877

[45] May 4, 1976

[54] HYDROFORMYLATION OF OLEFINS

[75] Inventor: Robert M. Gipson, Austin, Tex.

[73] Assignee: Jefferson Chemical Co., Inc., Houston, Tex.

[22] Filed: June 7, 1974

[21] Appl. No.: 477,268

Related U.S. Application Data

[63] Continuation of Ser. No. 674,767, Oct. 12, 1967, abandoned.

[52] U.S. Cl. ............... 260/604 HF; 260/632 HF; 252/431 R; 252/431C; 252/431 P
[51] Int. Cl.² ............... C07C 45/02; C07C 29/16
[58] Field of Search ............ 260/604 HF, 638 HF, 260/632 HF; 252/431 P

[56] References Cited
UNITED STATES PATENTS

| | | | |
|---|---|---|---|
| 3,488,334 | 1/1970 | Bayer et al. | 252/431 P X |
| 3,574,766 | 4/1971 | Meyer et al. | 260/601 R X |
| 3,640,898 | 2/1972 | Chung Liong So | 252/431 P X |

*Primary Examiner*—James O. Thomas, Jr.
*Assistant Examiner*—G. Breitenstein
*Attorney, Agent, or Firm*—Carl G. Ries; John R. Kirk, Jr.; James L. Bailey

[57] ABSTRACT

In the hydroformylation, or oxo, reaction, where olefins are reacted with carbon monoxide and hydrogen in the presence of a Group VIII metal complex catalyst to form aldehydes and alcohols, the catalyst can be advantageously modified by complexing it with an organic compound of pentavalent phosphorus, arsenic or antimony, as a ligand. When these compounds are used as the catalyst modifier, or ligand, in the reaction, a stable catalyst results which allows the oxo alcohols and aldehydes to be readily recovered from the reaction product without a special treatment to remove the catalyst metal. Furthermore, the catalyst-containing residues can be recycled for subsequent use in the hydroformylation reaction without a substantial impairment of the yields from these reactions. The ligand is incorporated into the catalyst complex in the proportion of about 0.5 to about 10 gram mols ligand per gram atom of the metal.

9 Claims, No Drawings

HYDROFORMYLATION OF OLEFINS

This is a continuation of application Ser. No. 674,767, filed Oct. 12, 1967, now abandoned.

BACKGROUND OF THE INVENTION

1. Field of the Invention

This invention relates to an improvement in the hydroformylation, or oxo, reaction wherein an olefin is reacted with carbon monoxide and hydrogen in the presence of a complex metal catalyst to form aldehydes and/or alcohols.

2. Description of the Prior Art

The hydroformylation, or oxo, reaction is well known in the art and comprises converting an olefin by reaction with carbon monoxide and hydrogen to aldehydes and/or alcohols having one or more carbon atom than the feedstock olefin. The reaction that takes place is an addition at the site of the double bond of the olefin by a hydrogen atom and a formyl group in the presence of a catalyst. Since the formyl group could add to either of the carbon atoms connected by the double bond, isomeric products result from this addition. The hydroformylation conditions of the reactions may be at a temperature of from 75° C. to about 250° C. at a pressure of from about 50 to about 10,000 psig. These hydroformylation conditions are widely used and well known to those in the art.

Many catalysts are known to be useful in the practice of this reaction, most of which comprise a metal from the Group VIII of the Periodic Table of Elements, in complex combination with carbon monoxide and various ligands. The most commonly used metals from this group are cobalt and rhodium. In the past, the most widely used catalyst for the oxo reaction has been dicobaltoctacarbonyl. This catalyst has been prepared from many forms of cobalt by reduction with hydrogen in the presence of carbon monoxide under pressure. However, this catalytic material suffers from several rather serious shortcomings such as its considerable instability during product separation, which precludes simple recovery of the catalyst for use in subsequent reactions. While chemical means exist for the recovery of the cobalt catalyst, they involve additional steps or reactions, increasing the complexity of the overall process and decreasing the commercial profitability of the same. Processes have been developed for the removal of the metal catalyst from the reaction products prior to the separation of the oxo aldehydes and alcohols, but this too is done with considerable difficulty.

In attempts to solve the problems inherent in the use of the metal complex catalyst, various ligands have been added to this complex catalyst mixture in attempts to stabilize the catalyst, both at the hydroformylation reaction conditions and conditions present during product separation. These attempts were made to enable those practicing the hydroformylation or oxo reactions to simply and economically recover the oxo products and recycle the catalyst containing residues for subsequent catalytic activity in the oxo reaction, while not sacrificing the yields of the oxo products by the production of increased reaction residues or production of unwanted by-products, such as paraffin hydrocarbons.

It has been attempted to use various modifiers for the complex catalyst to make it more stable to reaction and product work-up conditions. Various organo compounds of trivalent Group V elements, principally trivalent organo phosphorus or organo arsenic compounds such as organo phosphines, aromatic phosphites and hydrocarbyl arsines, have been complexed with various of the Group VIII metals to form a catalyst for the hydroformylation reaction.

It was previously thought that in order to successfully perform as a ligand in a complex catalyst system for the oxo reaction the compound must have a pair of electrons capable of forming a coordinate bond with the metal atom being complexed and simultaneously having the ability to accept electrons from the metal. The ligands contemplated by the prior art were organo compounds of trivalent phosphorus, arsenic or antimony, containing the trivalent atom having the electronic configuration thought to be necessary for the formation of stable coordinate bonds with the metal. Even when the above requirements for the ligand compound were met, much was left to be desired as far as performance of the complex catalyst was concerned.

However, in spite of the many attempts at improvement, the oxo reaction in the presence of these complex catalyst systems exhibits various problems, such a lack of catalyst stability at reaction and work-up conditions and the inability to recover the catalyst for reuse directly from the reaction products. It is a further disadvantage inherent in the prior art hydroformylation reaction involving mono alpha olefins that there is a relative inability to direct the reactions to the production of a predominantly terminal product when the olefin contains more than two carbon atoms.

While some of the prior art ligands modify the metal catalyst to the point where a predominantly aldehyde product can be produced, their success has been hampered by the inability to achieve high conversion of the olefin to the aldehyde. In addition, it was difficult to recover the aldehyde products from the catalyst-containing residue. Additionally, where emphasis was on high alcohol yields, prior art processes produce an undesirably high amount of paraffin hydrocarbon by-product.

It is therefore an object of the present invention to provide an improved hydroformylation, or oxo process, enabling the more efficient production and recovery of aldehydes and/or alcohols by the catalytic reaction of olefinic compounds with carbon monoxide and hydrogen in the presence of an improved hydroformylation catalyst.

Another object of my invention is the provision of an improved hydroformylation process enabling the efficient recovery by simple distillation of the alcohol and/or aldehyde product from the hydroformylation catalyst which is then recycled for further catalytic reaction in a subsequent hydroformylation reaction.

Still another object of my invention is the provision of an improved hydroformylation process enabling the variance of the relative proportions of the aldehyde and alcohol oxo products while reducing the formation of paraffin by-products.

Still another object of my invention is the provision of an improved hydroformylation catalyst which is stable to hydroformylation reaction conditions and product separation conditions.

Still another object of my invention is the provision of an improved hydroformylation catalyst which, though still mixed with reaction residues, retains its catalytic activity subsequent to the separation of the oxo alcohols and/or aldehydes.

Other objects and advantages of my invention will become apparent to those skilled in the art from the following description thereof.

SUMMARY OF THE INVENTION

This invention is directed to performing the hydroformylation, or oxo reaction, wherein an olefin is reacted with carbon monoxide and hydrogen to produce aldehydes and alcohols at hydroformylation temperatures and pressures in the presence of a complex Group VIII metal catalyst modified by incorporating therein a catalyst modifier of pentavalent phosphorus arsenic or antimony. These catalyst modifying ligands are characterized by the structure:

$x$, $y$ and $z = 0 - 3$ where
$x + y + z = 3$
$a = 1$ to 2
$b = 0$ to 1

$L = -CN$, $-OH$ or

M = phosphorus, arsenic or antimony
X = oxygen or sulfur
R, R' and R'' = aryl, alkyl, aralkyl alkaryl, or mixtures thereof having from one to about 20 carbon atoms.

The ligand of my invention may be referred to as a pentavalent ligand because the phosphorus, arsenic and/or antimony is in its pentavalent state. When this ligand is used to modify the complex metal catalyst at hydroformylation reaction conditions, highly satisfactory yields of the aldehyde and alcohol oxo product are obtained. In addition, the catalyst modified by the ligand of my invention reduces the amount of undesirable paraffin and hydrocarbon by-product which had been an inherent disadvantage of prior art hydroformylation reaction processes. It is frequently desirable that the oxo aldehyde product predominate, since the aldehyde is generally more chemically reactive than the alcohol and therefore a more valuable chemical intermediate. However, it is possible to vary the proportions of aldehyde and alcohols produced by altering the reaction conditions such as temperature, pressure and the hydrogen to carbon monoxide ratio in the synthesis gas. When the catalyst complex modified by the ligand of my invention is employed, the disadvantages of high paraffin formation when alcohols are desired and low olefin conversion when aldehyde is desired are avoided.

While it was previously thought, as mentioned above, that the compound of the trivalent element was necessary in order to perform successfully as a ligand in modifying the complex catalyst system of the oxo reaction, I have discovered that the compounds of pentavalent phosphorus, arsenic and antimony give high conversion, excellent yields and superb selectivity of products. The ligand of my invention gives the added advantage of producing a complex oxo catalyst which is quite stable and easily recovered from the hydroformylation reaction products in a readily reusable form by simple distillation to remove unreacted olefin and the aldehyde and alcohol products. The residue from this distillation contains the catalyst which may be used simply by recycling this residue to a hydroformylation reactor. It is not necessary to go through a complicated procedure for the recovery of the metal, followed by a conversion of the metal to the active complex in order to recover the reusable catalyst.

DESCRIPTION OF THE PREFERRED EMBODIMENTS

The practice of this invention relates to the well known hydroformylation, or oxo, reaction wherein an olefin is converted to an aldehyde or alcohol having one more carbon atom by reaction with a carbon monoxide and hydrogen synthesis gas in the presence of a Group VIII metal complex catalyst; the Group VIII metals being defined as shown on the Periodic Chart of Elements facing page 1 of *The Condensed Chemical Directory*, 7th Edition, Reinhold Publishing Corporation, New York, N. Y.

The hydroformylation reaction conditions are well known to those skilled in the art and are variable over wide ranges of temperatures and pressures. In the practice of this invention, the temperatures may range between from about 100° C. to about 300° C. with a preferred range being between 120° C. and about 200° C. The hydroformylation reaction pressures vary widely from about atmospheric to about 10,000 psig. A preferred range for the practice of my invention is from about 500 to about 10,000 psig., and an especially preferred range of about 1,500 to about 4,000 psig.

The ratio of the hydrogen to carbon monoxide in the synthesis gas may be varied according to the particular olefin being hydroformylated and the other reaction conditions present. Varying the hydrogen to carbon monoxide ratio has also been known in the art. Generally, the ratio of hydrogen to carbon monoxide will be at least 0.5 to 1, but it has been found in many cases that the rate of reaction as well as the yield of the desired product may be increased by increasing the hydrogen to carbon monoxide ratio to about 2 to 1, although ratios up to about 10 to 1, or more, have been used.

While the synthesis gas, the hydrogen and carbon monoxide, are usually present in a molar excess with respect to the olefin being hydroformylated, this ratio also may vary over very wide ranges but is usually employed within the range of 1 to 1 to about 10 to 1, with a preferred range for the practice of my invention from about 1 to 1 to about 2 to 1.

The reaction is performed in the presence of a complex metal catalyst formed by the interaction of a Group VIII metal with carbon monoxide and a catalyst-modifying ligand. Preferred Group VIII metals are cobalt, iron, rhodium, platinum, osmium and iridium with the especially preferred metals being cobalt and rhodium. In preparing the complex catalyst, the Group VIII metal may be introduced in the form of virtually any compound of the metal. Suitable metal salts comprise, for example, the carboxylates, such as acetates, octoates, and so forth, as well as the mineral acid salts, such as chlorides, sulfates, sulfonates, and so forth, of the suitable Group VIII metal.

The metals are present in a reaction medium which is comprised generally of the olefin, hydrogen, carbon monoxide, a solvent, when desired, and a catalyst complex modifying ligand. While the exact interaction of this ligand and the metal in the complex is not known, it is employed to enhance the metal as a hydroformylation catalyst to improve product results.

The ratio of catalyst to the olefin to be hydroformylated is generally not critical and may vary widely within the scope of this invention. The Group VIII metal may be present in quantities from about 0.005% to about 1 wt. % based upon the olefin charge. A preferred range is about 0.03% to about 0.5 wt. % based on the olefin charged, but said limits are practical only and catalytic amounts are not critical. The upper limit particularly is not critical but will be determined usually by economic consideration and solubility of the metal compound in the reaction medium. Inert solvents may be used to insure a substantially homogeneous all reaction medium, but are not necessary to the successful performance of the reaction.

While no solvent is necessary solvents which are inert with respect to the catalyst, as well as the olefin and hydroformylation products, may be present in the liquid reaction media. Inert solvents of this nature are well known to those skilled in the art. As illustrations, however, of useful inert solvents mention may be made of the aromatic hydrocarbons, such as benzene, xylene, toluene and their substituted derivatives, saturated aliphatic hydrocarbons, such as pentanes, naphtha, kerosene, mineral oils, etc.; saturated alicyclic hydrocarbons such as cyclohexane, cyclopentane, etc., as well as ethers, esters, etheresters, alcohols and ketones. Examples of preferred solvents include benzene, toluene, ethanol, isopropanol, ethylene glycol monomethylether and ethylene glycol dimethylether. It may also be advantageous to use a mixed solvent system, such as, for example, a mixture of benzene and ethanol.

While the prior art has taught modifiers for the Group VIII metal catalyst for the hydroformylation reaction in the form of trivalent ligands, such as phosphines, phosphites, arsines and stibines, I have discovered that compounds of pentavalent phosphorous, arsenic and antimony as defined generally by the structure:

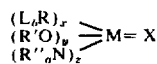

where
x, y and z = 0 - 3
x + y + z = 3
a = 1 to 2
b = 0 to 1
L = —CN, —OH
or

M = phosphorus, arsenic or antimony
X = oxygen or sulfur
R, R' and R'' = aryl, alkyl, aralkyl alkaryl, or mixtures thereof having from one to about 20 carbon atoms, modify the catalyst to form a system surprisingly adapted to use as a modified complex catalyst for the oxo reaction while remaining in a surprisingly stable catalytic state during the reaction and subsequent product work-up conditions.

Since the exact composition of the catalytically active complex is unknown, it will be referred to for purposes of this application as a complex comprising a Group VIII metal and a ligand of pentavalent phosphorous, arsenic or antimony. This description is used since both the metal and ligand are essential components of the complex, while the identity of all the other components is not exactly known. It is to be understood, however, that this description is intended to include any other components as described, such as carbon monoxide, that are also part of the active catalyst complex.

In the suitable ligands for the practice of my invention any essentially organic derivative of pentavalent phosphorous, arsenic or antimony is a suitable ligand for the complex catalyst of the present invention. While organinc radicals of any size and composition may be bonded to the pentavalent atom, those especially contemplated within the scope of this invention are the oxides and the sulfides of pentavalent phosphorus, antimony and arsenic, having attached thereto organic radicals as hereinbefore described. Each R group selected from the group of organic radicals denominated herein may be of any size, but it is especially preferred that they contain 1 to 20 carbon atoms. Moreover, the R groups in the compound may be the same or they may be a combination of more than one of the radicals, therefore, mixtures of the above-mentioned organic radicals are suitably bonded to the pentavalent phosphorus, arsenic or antimony atom either directly or through an oxygen, sulfur or nitrogen atom. It is to be further understood that when one or more of the R groups in an alkyl radical, that this radical may be further substituted with a functional group, such as a hydroxyl, carboxylic or cyano group, for example.

Some examples of compounds falling into the above-mentioned general classification are the phosphine oxides, phosphates, phosphonates, phosphoramides, phosphinesulfides, thiophosphates, arsine oxides and stibine oxides.

In addition to the above-mentioned compounds, it is also suitable for an organic radical to satisfy more than one of the valences of the phosphorus, arsenic or antimony atoms, thereby forming a heterocyclic compound with the pentavalent atom in the ring. For example, an alkylene radical may satisfy two phosphorus, arsenic or antimony valences with its two open valences and thereby form a cyclic compound. In this example, the third valence of the pentavalent atom may be satisfied by any one of the other organic radicals.

Another type of structure involving the pentavalent atom is called a bidentate ligand when two such phosphorous, arsenic or antimony atoms are present; a tridentate ligand when three such atoms are present, etc. Examples of these polydentate ligands include such structures as:

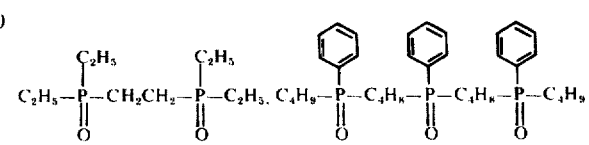

and the like.

The exact composition of the complex catalyst is not known. It appears that the catalytically active complex may contain, in addition to the Group VIII metal and the ligand, one or more substituents, such as carbon monoxide, hydrogen, the olefin and the anion of the metal salt used.

Specific examples of some preferred ligands for modifying the complex metal catalyst are, for example, trioctylphosphine oxide, tris-(cyanoethyl)-phosphine oxide, triethylphosphate, triphenylphosphine oxide, hexamethylphosphoroamide, tributylphosphine sulfide, triethylphosphate, tri-o-tolyl phosphate, triphenylphosphine sulfide, triphenylarsine oxide, triphenylstibine oxide, tributylphosphine oxide, diamyl amylphosphonate, trimethylphosphorothionate, triphenylphosphoramide, tribenzylphosphoramide, trimethylphosphate, triethylphosphate, tri-o-tolylthiophosphate and dimethylbenzylphosphonate.

The quantity of the ligand to be employed in the complex catalyst is based upon the amount of Group VIII metal in the reaction medium. Generally, in the practice of my invention, 0.5 gram mol to about 10 gram mols of the ligand is employed per gram atom of the Group VIII metal used. An especially preferred range is from 1 to about 3 gram mols ligand per gram atom of the metal. It is to be understood that when the terms gram mols and gram atoms are used in this specification, that any other mol weight equivalent is also intended to be included and that the important consideration is the molar ratio between the ligand and the Group VIII metal.

My invention is generally applicable to the hydroformylation of any aliphatic or cycloaliphatic compound having at least one ethylenic carbon-to-carbon bond. Catalysts modified by the ligand of my invention are advantageously used in the hydroformylation of these ethylenically unsaturated carbon-to-carbon linkages in hydrocarbons, especially those hydrocarbons having from 2 to 24 carbon atoms. The ethylenically unsaturated hydrocarbons may include both branched and straight-chain compounds having one or more olefinic sites which, in the case of more than one site, may be either conjugated or nonconjugated polyolefins. The olefinic site may be between the terminal carbon atom and its adjacent carbon atom or it may be an interior olefinic unsaturation; that is to say, the double bond being at a place other than between the terminal carbon atom and its adjacent carbon atom. It is not necessary that the olefin feedstock for the practice of hydroformylation reaction is the presence of a catalyst modified by the ligand of my invention to be a straight or branched chain hydrocarbon, for it is equally applicable to the cyclic olefins containing carbon-to-carbon unsaturation such as the cycloalkenes of which cyclohexene, cycloheptene and 1,5-cyclooctadiene mentioned as examples. Nor is the practice of this invention limited to the monocyclic olefins, but include the fused ring polycyclic olefins, such as cholestene.

The process of my invention may also be used to hydroformylate olefinically unsaturated alcohols, aldehydes and acids having a carbon-to-carbon atom olefinic bond in the molecule. It is also within the scope of my invention to hydroformylate mixtures of any of the above-mentioned olefinic hydrocarbons, such as a mixture of decene and dodecene.

Olefinic hydrocarbons such as, for example, polymeric olefinic fractions, cracked wax fractions an the like, containing substantial proportions of internal olefins are readily hydroformylated to fractions of hydroformylation, or oxo products, which are made up for the most part of mixtures of terminal aldehydes and alcohols having one more carbon atom than the olefins charged to the hydroformylation reaction.

It is especially preferred to practice the process of my invention in the hydroformylation of mono-olefins having from about 2 to 24 carbon atoms which have the olefinic bond between the terminal carbon atom and an adjacent carbon atom. Such olefinic hydrocarbons are known broadly as alpha olefins. It is from these feedstocks that many highly useful aldehydes and acohols are produced. When produced by the hydroformylation reaction employing a complex catalyst modified with the ligand of my invention, the advantages of my invention are singularly important.

In the prior art, when it was desired to produce predominantly the alcohol product, the complex catalyst used was usually such a strong hydrogenation catalyst that a high percentage of saturated paraffin hydrocarbon was produced in addition to the oxo alcohols which were desired. This paraffinic production produced a consequent reduction in the yield of the desired product. When those practicing the prior art desired to produce a predominantly aldehyde product, it was necessary to use a catalyst which, though producing the desired product, failed to give sufficiently high conversion of the olefins.

Sometimes, as indicated in the prior art, it is desirable to direct the reaction of the carbon atom to the terminal carbon atom in the olefin in order to form linear, or normal, alcohols. The production of a linear product was usually accompanied by a drop in conversion of the olefin to the aldehyde or alcohol. When catalysts, modified by the ligand of my invention, are used, conversion can be maintained at high levels while producing linear oxo products. It is a signal advantage of the catalyst modified by the ligand of my invention that either high aldehyde or high alcohol yields may be obtained without the consequent disadvantages exhibited by the prior art catalyst.

It is also beneficial to use a complex catalyst modified by the ligand of my invention is that it is extremely stable in the presence of hydroformylation reaction conditions as well as the conditions present during product separation and work-up, making it possible to recover virtually quantitatively all of the cobalt complex catalyst used in the hydroformylation reaction without resorting to special recovery techniques. The prior art fails to meet the needs of continuous reactions in this very important respect. The oxo products produced in the practice of my invention are readily separated from the other reaction products in a separation zone by a simple distillation, making it possible to simply recycle catalyst-containing residues to the reaction zone to be used as catalyst for subsequent hydroformylation reactions. In fact, I have discovered that in many instances upon recycle, even more advantageous yields result. Previously, the distillation of the oxo reaction product, in many cases destroyed the cobalt catalyst through precipitation of the metal into an insoluble mass. Such is not the case with the catalyst of my invention, which is easily recovered as mentioned above in the hydroformylation reaction residues and reused to catalyze subsequent reactions.

The complex catalyst modified by the ligand of my invention may be prepared in situ by the addition of the Group VIII metal compound and the modifying ligand of my invention to the hydroformylation reactor, followed by the introduction of carbon monoxide, hydrogen and olefin under normal hydroformylation conditions. Thus, the synthesis gas when first charged forms the complex catalyst and then the hydroformylation reaction follows. This works well in the batch process where the reactants and the reaction medium are charged to a closed autoclave and the entire reaction is performed therein. In practicing this invention in this manner, the complex catalyst is formed and the hydroformylation reaction carried out in the same vessel when the carbon monoxide and hydrogen mixture is charged.

Another way of practicing the hydroformylation reaction within the scope of my invention is by preforming the catalyst by treating the catalyst component of the Group VIII metal compound and the ligand dissolved in a solvent with hydrogen and carbon monoxide. This preformed catalyst then would be added to the feedstock and the hydroformylation reaction would proceed through the addition of the synthesis gas at hydroformylation conditions.

A third way of forming the catalyst is by mixing a metal carbonyl, usually dicobalt octacarbonyl, and the desired ligand, to form a complex. This intermediate complex is then charged to the reaction mixture containing the olefin to catalyze the reaction of the olefin with hydrogen and carbon monoxide when hydroformylation reaction conditions are present in the reaction vessel.

Therefore, it can be seen from the above discussion of the methods of performing the hydroformylation reaction within the scope of my invention, that the catalyst may either be formed in situ or it may be preformed and then charged to the reaction medium. After the reaction is completed, the hydroformylation, or oxo, aldehydes and/or alcohols are removed by a simply distillation or some other appropriate means. Then the residue containing the catalyst complex can be recycled and reused in a subsequent hydroformylation reaction without a detrimental effect to the conversion, yields or selectivity.

This invention will be further illustrated by the following examples which are intended to be illustrative only and are not to be construed to place limitations on the scope of this invention. In most of the examples which follow, octene-1 has been selected as a typical olefin. It will be understood, however, that the complex catalysts modified by the ligand of my invention used in the hydroformylation of octene-1 are also equally suitable to the hydroformylation of the other olefins hereinbefore mentioned.

EXAMPLE I

A 1,400 ml. rocking autoclave was charged with 250 g. 1-octene, 200 g. benzene, 3.5 millimols cobalt 2-ethyl hexoate and 4.5 millimols of trioctylphosphine oxide. The reactor was pressured to 2,000 psig. with a 1:1 mixture of hydrogen and carbon monoxide and heated to 200° C. The reaction temperature was maintained at 200°–217° C. and the pressure between 850 and 3,000 psig. for 2.5 hours. The reactor effluent was distilled to give 5 g. of $C_9$ aldehydes, 220 g. of $C_9$ alcohols and 45 g. of residue. The catalyst complex was formed in the reaction vessel in presence of the 1-octene reactant.

EXAMPLE II 40 g. of residue obtained from the distillation in Example I, 250 g. 1-octene and 160 g. benzene were charged to a 1,400 ml. autoclave and treated with 1:1 $H_2$:CO at 184°–201° C. and 1,100–3,000 psig. for 3.0 hours. Distillation of the reactor effluent gave 21 g. $C_9$ aldehydes, 193 g. $C_9$ alcohols and 74 g. additional residue. This illustrates the capacity to reuse the catalyst of this invention.

EXAMPLE III

A 1,400 ml. autoclave was charged with 250 g. 1-octene, 50 g. benzene, 50 g. ethanol, 0.138 g. rhodium trichloride and 1.0 g. trioctylphosphine oxide. This mixture was treated with 1:1 $H_2$:CO at 128°–133° and 1,800–3,000 psig. for 1.2 hours. Distillation of the reactor effluent gave 251 g. $C_9$ aldehydes, 19.9 g. of $C_9$ alcohols and 12 g. of residue.

The Examples IV through XII given in Table 1 below were obtained using the method of Example I. In each case 250 g. 1-octene, 200 g. benzene and 1:1 $H_2$:CO were used with different pentavalent organo compounds as the pentavalent ligands. These examples illustrate the applicability of these ligands in forming successful complex catalyst for the oxo reaction.

TABLE 1

| Example | Cobalt 2-ethyl hexoate millimols | Ligand (millimols) | Temp., °C. | Pressure, psig. | Time, hrs. | $C_9$ aldehydes | $C_9$ alcohols | Residue |
|---|---|---|---|---|---|---|---|---|
| IV | 4.5 | Tris-(cyanoethyl)-phosphine oxide (4.5) | 190–226° | 1650–3350 | 2.3 | 11 | 216 | 52 |
| V | 2.5 | Triethylphosphate (3.0) | 189–214° | 800–3225 | 1.25 | 44 | 153 | 74 |
| VI | 2.5 | Triphenylphosphine oxide (3.0) | 188–213° | 700–3000 | 2.0 | 61 | 141 | 77 |
| VII | 2.5 | Hexamethylphosphoramide (3.2) | 190–213° | 800–3150 | 3.0 | 31 | 175 | 67 |
| VIII | 2.5 | Tributylphosphine sulfide (5.0) | 190° | 2100–3000 | 3.0 | 154 | 60 | 22 |
| IX | 4.0 | Triethylphosphate (10) | 188–230° | 1600–3125 | 2.25 | 5 | 209 | 36 |
| X | 4.0 | Tri-o-tolyl-phosphate (8.0) | 190–225° | 1350–3300 | 1.5 | 45 | 150 | 62 |
| XI | 2.5 | Triphenylphosphine sulfide (5.0) | 190–205° | 1900–3250 | 3.0 | 197 | 17 | 28 |
| XII | 2.5 | Triphenylarsine oxide (5.0) | 190–214° | 1400–3300 | 3.0 | 182 | 48 | 47 |

EXAMPLE XIII

A 1,400 ml. rocking autoclave was charged with 4.2 millimols cobalt 2-ethylhexoate, 9 millimols tributylphosphine oxide and 200 g. toluene. The reactor was pressured to 2,500 psig. with 1:1 H₂:CO and heated at 190° C. for 2 hours to form the modified complex catalyst. The reactor was cooled and vented and 250 g. 1-octene was added. This reaction mixture was treated with 1:1 H$_2$:CO at 150°–160° C. and 500–3,000 psig. for 2 hours. Distillation of the reactor effluent gave 178 g. C$_9$ aldehydes, 31 g. of C$_9$ alcohols, 7.5 g. paraffin, 0.5 g. unreacted olefin and 90 g. of residue. This example illustrates the technique of preforming the complex catalyst and then conducting the hydroformylation reaction.

EXAMPLE XIV

The residue from the distillation in Example XIII, 250 g. 1-octene and 100 g. benzene were charged to 1,400-ml. autoclave. This mixture was treated with 1:1 H$_2$:CO at 188°–192° C. and 700–3,000 psig. for 2.35 hours. The reactor effluent was distilled to give 17 g. C$_9$ aldehydes, 148 g. C$_9$ alcohols 10 g. paraffin, 0.3 g. unreacted olefin and an additional 125 g. of residue. This illustrated that the preformed catalyst of my invention is also useful in continuous reactions where the catalyst is recycled.

EXAMPLE XV

A 1,400 ml. rocking autoclave was charged with 4 millimols cobalt 2-ethylhexoate, 8 millimols amy diamylphosphonate and 200 g. benzene. This solution was treated with 1:1 H$_2$:CO at 188°–190° C. and 4,000–4,025 psig. for 2 hours. The reactor was cooled and vented and 250 g. 1-octene was added to the autoclave. The reaction mixture was treated with 1:1 H$_2$:CO at 150°–156° C. and 1,200–3,000 psig. for 2 hours. Distillation of the reactor effluent gave 210 g. C$_9$ aldehydes, 9 g. C$_9$ alcohols, 8 g. paraffin, 3.7 g. unreacted olefin and 79 g. residue.

EXAMPLE XVI

The residue obtained from the distillation of oxo products in Example XV and 120 g. benzene were added to a 1,400 ml. autoclave and treated with 1:1 H$_2$:CO at 170° C. and 3,750 psig. for 1 hour. The autoclave was cooled and vented and 250 g. 1-octene was added. The reaction mixture was treated with 1:1 H$_2$:CO at 148°–159° C. and 1,000–3,000 psig. for 2 hours. The reactor effluent was distilled to give 234 g. C$_9$ aldehydes, 6 g. C$_9$ alcohols, 8.5 g. paraffin, 5 g. unreacted olefin and an additional 32 g. of residue.

EXAMPLE XVII

A 1,400 ml. rocking autoclave was charged with a solution consisting of 250 g. 1-octene, 250 g. toluene, 4 millimols of dicobalt octacarbonyl and 6 millimols of tributylphosphine oxide. This mixture was treated with 1:1 H$_2$:CO at 148°–158° C. and 1,800–3,000 psig. for 2.3 hours. Distillation of the reactor effluent gave 200 g. of C$_9$ aldehydes, 13 g. of C$_9$ alcohols and 73 g. of residue.

EXAMPLE XVIII

Cobalt 2-ethylhexoate and tributylphosphine oxide, in a mol ratio of 1:2, were dissolved in benzene to a concentration of 0.08 wt. % cobalt. This solution and octene-1 were fed in equal weights to a continuous reactor at a total liquid feed rate of 948 g. per hour per liter of reactor volume along with an excess of 1:1 H$_2$:CO. The temperature of the reaction was 175° C. and the pressure was 3,000 psig. The reactor effluent was distilled to remove the unreacted olefin and oxo products overhead, separating the products from the solvent and catalyst-containing residue. The results of the process are indicated in Table 2.

TABLE 2

|  | Mol % |
|---|---|
| Conversion of olefin | 93 |
| Yield of oxo products | 89 |
| Aldehydes | 90 |
| Alcohols | 10 |
| Yield of paraffin | 3 |
| Normal aldehydes | 64 |

This indicates the applicability of the complex catalyst modified by the ligand of my invention for use to produce predominately high-aldehyde product and still maintaining high conversion of the olefin charged.

EXAMPLE XIX

Following generally the procedure of Example XVIII, the following continuous reactions were run for comparison of the catalyst modified with the ligand of my invention with prior art complex catalyst systems. The olefin charged is octene-1 and the reaction conditions and results are shown on Table 3.

TABLE 3

| Catalyst | Unmodified cobalt octacarbonyl | Cobalt: tributyl- phosphine complex | Cobalt: tributyl- phosphine complex | Cobalt: triethyl- phosphate complex | Cobalt: tributyl- phosphine oxide complex | Cobalt: trioctyl- phosphine oxide complex | Cobalt: tri-o-tolyl- phosphate complex |
|---|---|---|---|---|---|---|---|
| Wt. % cobalt based on olefin | 0.40 | 0.08 | 0.17 | 0.066 | 0.10 | 0.06 | 0.11 |
| Liquid feed rate g./hr./l. | 805 | 606 | 746 | 1116 | 962 | 758 | 1162 |
| Temperature, °C. | 140 | 190 | 200 | 160 | 190 | 175 | 160 |
| Pressure, psig. | 3000 | 3000 | 750 | 3000 | 3000 | 3000 | 3000 |
| Synthesis gas: H$_2$:CO | 1:1 | 1:1 | 2:1 | 1:1 | 1:1 | 1:1 | 1:1 |
| Conversion, mol % | 96 | 54 | 24 | 80 | 97 | 91 | 86 |
| Yield C$_9$ oxo products, mol % | 83 | 91 | 82 | 94 | 81 | 88 | 91 |
| Yield paraffin, mol % | 4 | 7 | 17 |  | 3 | 3 | 2 |
| Normal products, % of olefin charged | 52.6 | 37.3 | 4.7 | 48.2 | 40.8 | 47.3 | 50.1 |
| Cobalt recovery, % | * | 79 | 24 | 88 | 99 | 92 | 81 |

*Metallic cobalt deposited in system

Examination of the data of Table 3 illustrates the high conversion, yield and selectivity of normal products obtainable when the catalyst modified by the ligand of my invention is used in the continuous reaction. Also, it will be noted that generally higher feed rates are possible, indicating higher reaction rates with this complex catalyst modified by the ligand of my invention, and that the catalyst is recoverable to a greater extent and paraffin hydrocarbon by-products are minimized.

EXAMPLE XX

A solution of 8 millimols of cobalt 2-ethylhexoate and 20 millimols of triethylphosphate in 200 ml. of benzene was treated in an autoclave with 1:1 $H_2$:CO mixture for one hour at 170° C. and 3,700–114 3,750 psig. The autoclave was cooled and vented, and 250 g. of 1,5-cyclooctadiene was added. This mixture was treated with 1:1 $H_2$:CO at 145°–185° C. and 1,800–3,000 psig. for 3 hours. Distillation of the reactor effluent gave 203 g. of hydroformylation products boiling at 36°–75° C. at 5 mm. Hg pressure and 79 g. of residue. Reduction of a portion of the distilled oxygenated products over a nickel-based catalyst with hydrogen at elevated temperatures and pressures gave a 90% yield of hydroxymethylcyclooctane.

EXAMPLE XXI

Similarly, the following olefins are hydroformylated in the presence of the complex catalyst of the reaction conditions set forth in the foregoing examples to aldehydes and alcohols having one more carbon atom than the olefin charged: propylene, decene, $C_{12}$–$C_{14}$ olefinic hydrocarbon fractions and 1-eicosene.

I claim:

1. The process for the production of aldehydes and alcohols comprising the steps of:
   a. Contacting in a reaction zone an olefin with hydrogen and carbon monoxide under hydroformylation conditions of 120°C to about 200°C and 1500 to 4000 psig pressure in the presence of a catalytic amount of a Group VIII metal complex catalyst thereby reacting to produce a reaction product including therein the aldehydes and alcohols, unreacted olefin and a catalyst-containing residue;
   b. Passing the reaction product to a separation zone;
   c. Distilling the reaction product into a vapor phase component comprising unreacted olefin, aldehydes and alcohols, and a liquid phase component including the catalyst-containing residue; and
   d. Recycling at least part of the catalyst-containing residue to the reaction zone;

wherein the Group VIII metal is in complex combination with carbon monoxide and 0.5 to about 10 g. mols of a ligand per gram atom of the Group VIII metal wherein the ligand is defined by the structure:

with the equation $x + y + z = 3$ being satisfied wherein $a$ is an integer from 1 to 2; $b$ is an integer from 0 to 1; M is selected from the group consisting of phosphorus and arsenic; X is selected from the group consisting of oxygen and sulfur; L is selected from the group consisting of —OH —CN, and

and R, R' and R'' are selected from the group consisting of alkyl, aryl, aralkyl, alkaryl and mixtures thereof having from 1 to about 20 carbon atoms provided that $b$ only when R is alkyl.

2. In the process for the production of aldehydes and alcohols which comprises contacting olefinic hydrocarbon with carbon monoxide and hydrogen at hydroformylation reaction conditions of 100°C. to 300°C. and about atmospheric to 10,000 psig pressure in the presence of a complex catalyst comprising a Group VIII metal and carbon monoxide, thereby reacting the olefinic hydrocarbon with the carbon monoxide and hydrogen with the formation of aldehydes and alcohols having one more carbon atom than the olefinic hydrocarbon, the improvement which comprises modifying the complex catalyst with a ligand represented by the structure:

with the equation $x + y + z = 3$ being satisfied wherein $x$, $y$ and $z$ are integers from 0 to 3; $a$ is an integer from 1 to 2; $b$ is an integer from 0 to 1; M is selected from the group consisting of phosphorus and arsenic; X is selected from the group consisting of oxygen and sulfur; L is selected from the group consisting of —CN, —OH and

and R, R' and R'' are selected from the group consisting of alkyl, aryl, aralkyl, alkaryl and mixtures thereof having from 1 to about 20 carbon atoms, provided that $b$ is 1 only when R is alkyl; wherein about 0.5 to about 10 g. mols of the ligand are present per gram atom of the Group VIII metal.

3. The method of claim 2, wherein the molar ratio of the ligand to the Group VIII metal is within the range of 1:1 and about 3:1.

4. The method of claim 2 wherein L is CN and R is an alkyl group when $b$ is equal to 1.

5. The method of claim 2 wherein said contacting is accomplished in the presence of an inert solvent.

6. The method of claim 2 wherein said olefinic hydrocarbon is selected from a group consisting of aliphatic and cycloaliphatic compounds having at least one ethylenic carbon-carbon bond and containing from 2 to about 24 carbon atoms.

7. The method of claim 2 wherein said ligand is selected from a group consisting of trioctylphosphine oxide, tris-(cyanoethyl)-phosphine oxide, triethylphosphate, triphenylphosphine oxide, hexamethylphosphoroamide, tributylphosphine sulfide, triethylphosphate, tri-o-tolyl phosphate, triphenylphosphine sulfide, triphenylarsine oxide, triphenylstibine oxide, tributylphosphine oxide, diamyl amylphosphonate, trimethylphosphorothionate, triphenylphosphoramide, tribenzylphosphoramide, trimethylphosphonate, triethylphosphate, tri-o-tolylthiophosphate and dimethylbenzylphosphonate.

8. The method of claim 2, wherein the Group VIII metal is selected from the group consisting of cobalt and rhodium.

9. The method of claim 8, wherein from about 1 to about 3 g. mols of the ligand is present per gram atom of the Group VIII metal.

* * * * *